(12) United States Patent
Kurumatani et al.

(10) Patent No.: US 6,340,693 B1
(45) Date of Patent: Jan. 22, 2002

(54) PROTECTIVE AGENT FOR NERVOUS SYSTEM STRUCTURAL CELLS

(75) Inventors: Hajimu Kurumatani; Susumu Matsuda; Mie Kainoh, all of Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/180,772

(22) PCT Filed: Mar. 12, 1998

(86) PCT No.: PCT/JP98/01028

§ 371 Date: Feb. 16, 1999

§ 102(e) Date: Feb. 16, 1999

(87) PCT Pub. No.: WO98/41209

PCT Pub. Date: Sep. 24, 1998

(30) Foreign Application Priority Data

Mar. 14, 1997 (JP) ............................................. 9-061489

(51) Int. Cl.$^7$ .................. A61K 31/44; A61K 31/34; A61K 31/385; A61K 31/35; C07D 333/02
(52) U.S. Cl. .................. 514/337; 514/468; 514/433; 514/444; 514/451; 549/29; 549/458; 549/356
(58) Field of Search .................. 549/458, 29, 356; 514/468, 451, 337, 433, 444

(56) References Cited

U.S. PATENT DOCUMENTS

| | | |
|---|---|---|
| 4,464,388 A | 8/1984 | Sakai et al. |
| 4,499,085 A | 2/1985 | Masuda |
| 5,086,071 A | 2/1992 | Ohno et al. |

FOREIGN PATENT DOCUMENTS

| | | | |
|---|---|---|---|
| JP | 57032277 | * | 2/1982 |
| JP | 2262519 A | | 10/1990 |

OTHER PUBLICATIONS

Hotta et al., *Diabetes,* Effects of Beraprost Sodium and Insulin on the Electroretinogram, Nerve Conduction, and Nerve Blood Flow in Rats with Streptozotocin–Induced Diabetes, vol. 45, pp. 361–366, (3/96).

Ueno et al., *Life Sciences,* Effects of Beraprost Sodium, A Prostacyclin Analogue, On Tail Flick Response in Two Models of Diabetic–Neuropathy In Rats and Its Mechanism, vol. 59, No. 9, pp. 105–110 (1996).

Kainoh et al., *Pharmacological Research,* Inhibitory Effect of Beraprost Sodium On Formation Of Lipid Peroxides In Ischemia And Recirculation–Induced Cerebral Injury, vol. 28, No. 3, (1993).

* cited by examiner

*Primary Examiner*—Alan L. Rotman
*Assistant Examiner*—Binta Robinson
(74) *Attorney, Agent, or Firm*—Birch, Stewart, Kolasch & Birch, LLP

(57) ABSTRACT

The present invention provides a protective agent for nervous system structural cells comprising a prostaglandin I derivative, preferably a prostaglandin $I_2$ derivative, particularly beraplost, as an active component. This medicine exhibits excellent effects as a protective agent for nervous system structural cells, and is effective as an excellent agent for preventing or curing cerebrovascular disorder, cerebral nerve cell disorder, ischemic cerebral disorder, dementia, and peripheral nerve disorder due to diabetic or the like.

11 Claims, 2 Drawing Sheets

PROTECTIVE AGENT FOR NERVOUS SYSTEM STRUCTURAL CELLS

This application claims the benefit under 35 U.S.C. §371 of prior PCT International Application No. PCT/JP98/01028 which has an International filing date of Mar. 12, 1998 which designated the United States of America, the entire contents of which are hereby incorporated by reference.

TECHNICAL FIELD

The present invention relates to a protective agent for nervous system structural cells comprising a prostaglandin I derivative or a salt thereof as an active ingredient.

BACKGROUND ART

Recently, cases of various cerebrovascular diseases have increases with the arrival of an aging society. Cerebrovascular diseases are considered to be caused by aging, hypertension, arterial sclerosis, hyper lipidemia, and the like, and are generally called as stroke. Causal diseases of stroke include cerebral infarction (cerebral thrombosis and cerebral embolus), cerebral hemorrhage and subarachnoid hemorrhage, as well as transient cerebral ischemic attack, herpertensive encephalopathy, and the like. These causal diseases cause ischemia and damage or death of the structural cells of the nervous system around the ischemic area, resulting in occurrence of local mental and nervous diseases such as cerebrovascular dementia. Also, cases of Alzheimer diseases as representative presenile dementia have increased. Alzheimer diseases are representative diseases of presenile dementia, and cause memory disorder and spatial and temporal disorientation, and sometimes cause symptoms such as aphasia, apraxia, and agnosia. These symptoms are characterized by overall disorder of cerebral functions, and dementia is advanced in the final stage, resulting in death from systemic hyposthenia. Pathologically, it is known that Alzheimer diseases cause extensive encephalatrophy, Alzheimer's neurofibrillary degeneration and senile plaque.

Although a cerebral circulation improving agent and a cerebral function improving agent have been used for improving psychoneurosis associated with cerebral nerve disorder and senile dementia, all medicines do not exhibit sufficient effect.

Peripheral nerve disorder is also called as multiple neuritis or neuritis, and occurs due to various causes such as heredity, trauma, intoxation, inflammation, metabolic disorder such as diabetic and the like, malignant tumors, peripheral nerve compression by a tumor, and the like. The symptoms of the peripheral nerve disorder include sensory disorder, motor disorder, hypomyotonia, areflexia, autonomic disorder, and the like, as well as showing a neurogentic pattern in an electromyogram and a decrease in peripheral nerve conduction velocity. Pathologic symptoms include nonspecific degeneration such as axonal degeneration, segmental demyelination, Waller degeneration, and the like. As a therapy, steroid, vitamin, an anti-inflammatory drug, an analgesic, and the like are used together with rehabilitation, but sufficient therapeutic effects cannot be obtained.

The above-described various diseases are due to a variety of causes, but various symptoms such as dementia as well as mental symptoms, sensory disorder, motor disorder, and autonomic disorder finally occur due to death, falling or functional disorder of the structural cells of the nervous system. Therefore, amelioration of disorder and improvement of these symptoms can be expected by strongly protecting the nerve cells. Furthermore, it has been made clear that nerve structural cells other than nerve cells, such as the above neuroglia and the like play a very important role in maintaining the function of the nerve cells, and amelioration of neuroglia disorder is effective in maintaining the function of the neuron.

Although prostaglandin derivatives are known to have various biological activities, they are classified in some groups according to modification of the 5-member ring comprising C-8 to C-12. Of these prostaglandin derivatives, compounds in which the carbon atoms at the 6- and 9-positions are combined through an oxygen atom are referred to as "PGI", and prostaglandin $I_2$ ($PGI_2$, prostacyclin) is known as a representative. $PGI_2$ is known as a substance having the action of suppressing platelet aggregation and the action of dilating peripheral vessels (refer to Nature, Vol. 268, p. 688, 1976).

As compounds in which instability of $PGI_2$ is significantly improved, Japanese Examined Patent Publication Nos. 2-12226, 2-57548 and 1-53672 disclose PGI derivatives having a skeleton in which the structure of the exoenol ether moiety characteristic of the structure of $PGI_2$ is converted into an inter-m-phenylene structure. Other known PGI derivatives include PGI derivatives in which the carbon atoms at the 6- and 9-positions are substituted by oxygen atoms, and PGI derivatives in which the oxygen atoms are substituted by carbon atoms or other hetero atoms. Examples of such derivatives include ataprost, ilopost, clinprost, ciprostene, naxaprostene, taprostene, cicaprost, pimilprost CH-169, and CS570 (refer to Gendai-Iryosha, "Generals of Prostaglandin" No. 1, p. 123, 1994; New Drugs of Tomorrow, p. 15-IV-185, 1996; New Drugs of Tomorrow, p. 15-III-551, 1996). However, it is unknown that these prostaglandin I derivatives have the action of protecting the structural cells of the nervous system.

An object of the present invention is to provide a protective agent exhibiting the strong action of protecting the structural cells of the cerebral and peripheral nervous system, and the excellent effect of preventing or curing cerebrovascular disorder, cerebral nerve cell disorder, ischemic cerebral disorder, dementia, and peripheral nerve disorder due to diabetic or the like.

DISCLOSURE OF INVENTION

The present invention provides a protective agent for nervous system structural cells, comprising, as an active ingredient, a prostaglandin I derivative, preferably a prostaglandin $I_2$ derivative.

BEST MODE FOR CARRYING OUT THE INVENTION

Figure 1:
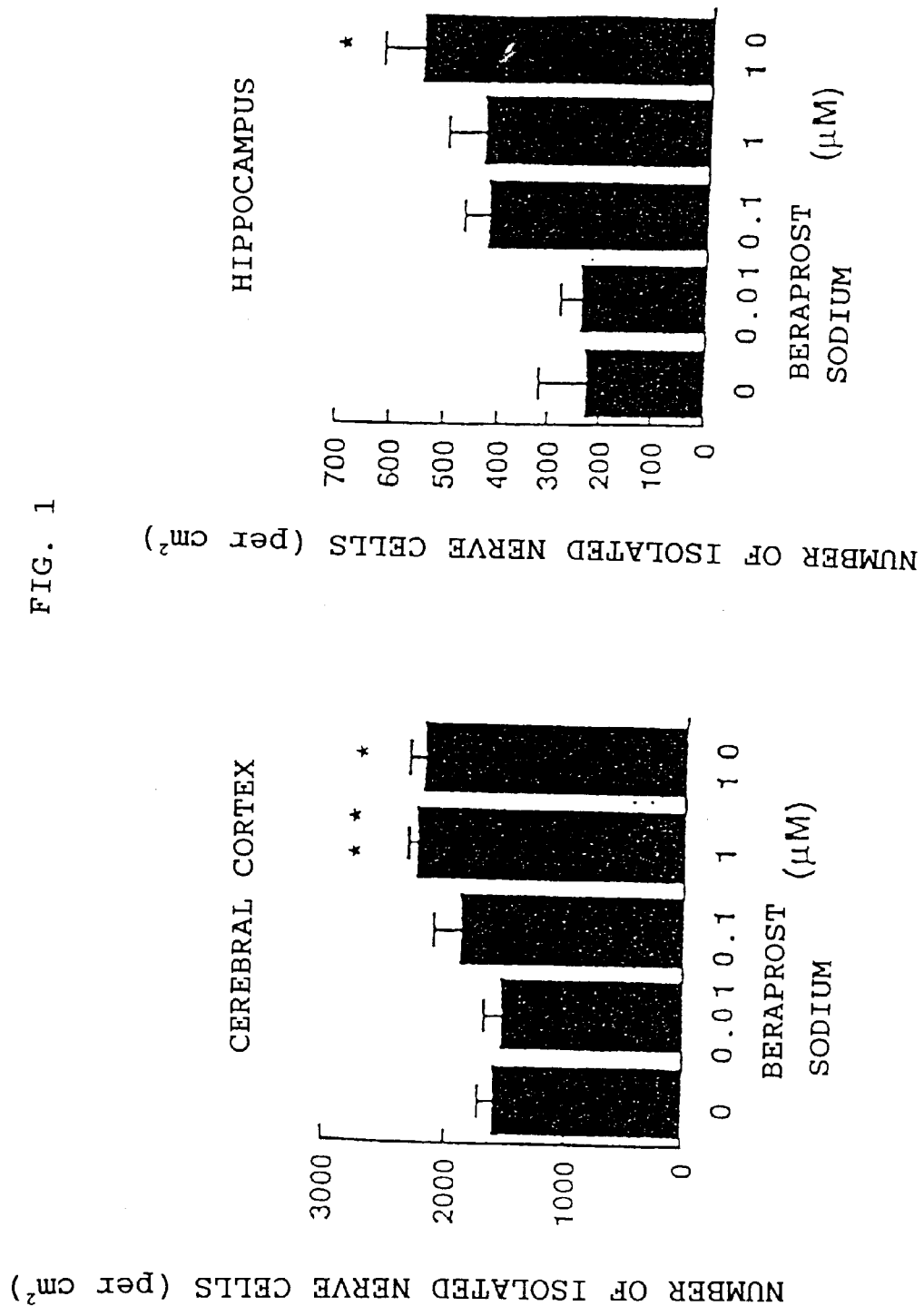
FIG. 1 is a graph showing the cytoprotective effect of beraprost sodium on cultured nerve cells.

As the prostaglandin I derivative of the present invention, any one of prostaglandin $I_1$ derivatives, prostaglandin $I_2$ derivatives, prostaglandin $I_3$ derivatives, or salts thereof may be used, but prostaglandin $I_2$ derivatives, or salts thereof are preferably used. More preferably, 4,8-inter-m-phenylene prostaglandin $I_2$ derivatives represented by the following formula (I) or pharmacologically acceptable salts thereof are used.

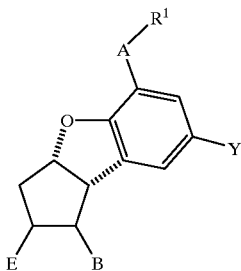

(I)

wherein R¹ represents the following:

(A) COOR² wherein R² is:

1) hydrogen or a pharmacologically acceptable cation;
2) straight chain alkyl having 1 to 12 carbon atoms, or branched-alkyl having 3 to 14 carbon atoms;
3) —Z—R³
wherein Z is a valence bond or straight chain or branched alkylene represented by $C_tH_{2t}$ wherein t represents an integer of 1 to 6, and R³ represents cycloalkyl having 3 to 12 carbon atoms or substituted cycloalkyl having 3 to 12 carbon atoms and 1 to 3 substituents R⁴ which is hydrogen or alkyl having 1 to 5 carbon atoms;
4) —(CH₂CH₂O)$_n$CH₃
wherein n is an integer of 1 to 5;
5) —Z—Ar¹
wherein Z is defined as the same as the above, and Ar₁ is phenyl, α-naphthyl, β-naphthyl, 2-pyridyl, 3-pyridyl, 4-pyridyl, α-furyl, β-furyl, α-thienyl, β-thienyl or substituted phenyl (wherein a substituent is at least one of chlorine, bromine, fluorine, iodine, trifluoromethyl, alkyl having 1 to 4 carbon atoms, nitro, cyano, methoxy, phenyl, phenoxy, p-acetamidobenzamide, —CH=N—NH—C(=O)—NH₂, —NH—C(=O)—Ph, —NH—C(=O)—CH₃ and —NH—C(=O)—NH₂);
6) —$C_tH_{2t}$COOR⁴
wherein $C_tH_{2t}$ and R⁴ are defined as the same as the above;
7) —$C_tH_{2t}$N(R⁴)₂
wherein $C_tH_{2t}$ and R⁴ are defined as the same as the above;
8) —CH(R⁵)—C(=O)—R⁶
wherein R⁵ is hydrogen or benzoyl, and R⁶ is phenyl, p-bromophenyl, p-chlorophenyl, p-biphenyl, p-nitrophenyl, p-benzamidophenyl, or 2-naphthyl;
9) —$C_pH_{2p}$—W—R⁷
wherein W is —CH=CH—, —CH=CR⁷ or —C≡C—, and R⁷ is hydrogen or straight chain or branched alkyl or aralkyl having 1 to 30 carbon atoms, and p is an integer of 1 to 5; or
10) —CH(CH₂OR⁸)₂
wherein R⁸ is alkyl or acyl having 1 to 30 carbon atoms;

(B) —CH₂OH;

(C) —C(=O)N(R⁹)₂
wherein R⁹ is hydrogen, straight chain alkyl having 1 to 12 carbon atoms, branched alkyl having 3 to 12 carbon atoms, cycloalkyl having 3 to 12 carbon atoms, cycloalkylalkylene having 4 to 13 carbon atoms, phenyl, substituted phenyl (wherein the substituent is defined as the same as in (A) 5)), aralkyl having 7 to 12 carbon atoms, or —SO₂R¹⁰ wherein R¹⁰ is alkyl having 1 to 10 carbon atoms, cycloalkyl having 3 to 12 carbon atoms, phenyl, substituted phenyl (the substituent is defined as the same as in (A) 5)), or aralkyl having 7 to 12 carbon atoms, two R⁹ groups may be the same or different, and when one of the R⁹ groups is —SO₂R¹⁰, the other R₉ is not —SO₂R¹⁰; or (D) —CH₂OTHP (THP is a tetrahydropyranyl group);

A is the following:
1) —(CH₂)$_m$—;
2) —CH=CH—CH₂—;
3) —CH₂—CH=CH—;
4) —CH₂—O—CH₂—;
5) —CH=CH—;
6) —O—CH₂—; or
7) —C≡C—;

wherein m represents an integer of 1 to 3;

Y is hydrogen, alkyl having 1 to 4 carbon atoms, chlorine, bromine, fluorine, formyl, methoxy or nitro;

B is —X—C(R¹¹)(R¹²)OR¹³
wherein R¹¹ is hydrogen, alkyl having 1 to 4 carbon atoms; R¹³ is hydrogen, acyl having 1 to 14 carbon atoms, aroyl having 6 to 15 carbon atoms, tetrahydropyranyl, tetrahydrofuranyl, 1-ethoxyethyl, or t-butyl; X is the following:
1) —CH₂—CH₂—;
2) —CH=CH—; or
3) —C≡C—; and R¹² is the following:
1) straight chain alkyl having 1 to 12 carbon atoms, or branched alkyl having 3 to 14 carbon atoms;
2) —Z—Ar²
wherein Z is the defined as the same -as the above, and Ar² represents phenyl, α-naphthyl, β-naphthyl, or phenyl substituted by at least one chlorine, bromine, fluorine, iodine, trifluoromethyl, alkyl having 1 to 4 carbon atoms, nitro, cyano, methoxy, phenyl or phenoxy;
3) —$C_tH_{2t}$OR¹⁴
wherein $C_tH_{2t}$ is defined as the same as the above, and R¹⁴ represents straight chain alkyl having 1 to 6 carbon atoms, branched alkyl having 3 to 6 carbon atoms, phenyl, phenyl substituted by at last one chlorine, bromine, fluorine, iodine, trifluoromethyl, alkyl having 1 to 4 carbon atoms, nitro, cyano, methoxy, phenyl or phenoxy, cyclopentyl, cyclohexyl, or cyclopentyl or cyclohexyl substituted by 1 to 4 straight chain alkyl groups having 1 to 4 carbon atoms;
4) —Z—R³
wherein Z and R³ are defined as the same as the above;
5) —$C_tH_{2t}$—CH=C(R¹⁵) R¹⁶
wherein $C_tH_{2t}$ is defined as the same as the above, and R¹⁵ and R¹⁶ each represent hydrogen, methyl, ethyl, propyl, or butyl; or
6) —$C_uH_{2u}$—C≡C—R¹⁷
wherein u is an integer of 1 to 7, $C_uH_{2u}$ represents straight chain or branched alkylene, and R¹⁷ represents straight chain alkyl having 1 to 6 carbon atoms;

E is hydrogen or —OR¹⁸
wherein R¹⁸ represents acyl having 1 to 12 carbon atoms, aroyl having 7 to 15 carbon atoms, or R² (wherein R² is defined as the same as the above); and
the formula represents the d, l or dl form.

Preferable examples of the prostaglandin I derivatives of the present invention include beraprost or salts thereof represented by the following formula:

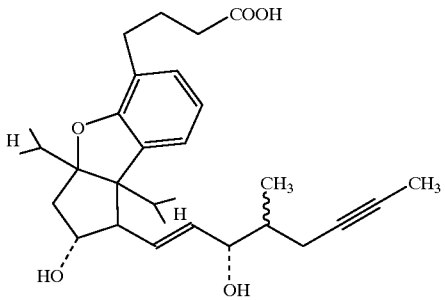

iloprost, clinprost, ataprost, ciprostene, naxaprostene, taprostene, cicaprost, pimilprost, CH-169, SM-10902, and the like, but the derivatives are not limited to these compounds.

The prostaglandin derivatives of the present invention can be produced by a known method. For example, compounds represented by the formula (I) can be produced by the method disclosed in Japanese Examined Patent Publication No. 1-53672.

In the present invention, the nervous system structural cells include nerve cells, oligodendrocytes, astrocytes, microglia, neuroglia such as ependymocytes, and neurosecretory cells in the brain; and nerve cells, Schwann cells, satellite cells, and paraneuron in the peripheral nerves. The protective agent for nervous system structural cells of the present invention is particularly effective for neuroglia and nerve cells.

The prostaglandin I derivatives of the present invention have the excellent protective action on the nervous system structural cells and is effective as an excellent agent for preventing or curing cerebrovascular disorder, cerebral neurocyte disorder, ischemic cerebral disorder, dementia, and peripheral nerve disorder due to diabetic or the like.

The prostaglandin I derivative of the present invention is administered 1 to 3 times a day in a dose of 0.01 to 100 mg/adult.

Although the protective agent for nervous system structural cells of the present invention may contain at least one prostaglandin I derivative or a salt thereof, the agent can also be orally administered in the form of a solid containing the additives below.

Examples of such additives include an excipient such as starch, lactose, sucrose, glucose, mannitol, potassium carbonate, calcium sulfate, or the like; a binder such as starch, dextrin, gum arabic, tragacanth, methyl cellulose, gelatin, polyvinyl pyrrolidone, polyvinyl alcohol, or the like; a disintegrator such as starch, polyvinyl pyrrolidone, crystalline cellulose, or the like; a lubricant such as magnesium stearate, talc, or the like; a colorant; a flavor; and the like.

The prostaglandin I derivatives of the present invention can be used in various forms. Examples of the forms include conventional forms such as a tablet, a sugar-coated tablet, a powder, granules, a troche, a capsule, a pill, a syrup, and the like.

The compounds may also be parenterally administered in the form of a sterilized solution, and another solute such as sodium chloride, glucose, or the like can also be used in an amount sufficient for making the solution isotonic.

The protective agent for nervous system structural cells of the present invention can be applied to the oral formulations as well as a wide range of parenteral formulations such as various injections, suppositories and the like.

EXAMPLES

Although the present invention will be described in detail below, the present invention is not limited to these examples.

Example 1

Effect of improving survival rate of cultured isolated nerve cells:

The protective effect of beraprost sodium on nerve cells was examined by using nerve cells derived from a rat fetus. The cerebral cortex and hippocampus were obtained from the brain of a rat fetus of 17 days age, and isolated nerve cells were obtained therefrom by trypsin and pipetting treatment. The thus-obtained cells were inoculated into a 48-well culture plate coated with polylysine at a cell concentration of $5 \times 10^3$ cells/cm$^2$; followed by culture in a DF medium containing no serum at 37° C. for 3 days. After completion of culture, the cells were fixed by formalin, and the number of cells having axons was measured under a microscope. Beraprost sodium was added in an amount of each of 1, 10 and 100 μM during culture.

The results are shown in FIG. 1 (In the figure, * and ** represent student t-test results. *: $p<0.05$ vs control. **: $p<0.01$ vs control. This applies to the description below). The nerve cells gradually died and fell under the conditions in this example, beraprost sodium prevented falling of the nerve cells, and increased the number of survival cells depending upon the concentration. This increase was significant in the cerebral cortex at 1 and 10 μM of beraprost sodium, and in the hippocampus at 10 μM of beraprost sodium.

Example 2

Human glioma cells were separated from a patient of glioma (male of 58 years old), and then subjected to subculture in a 10% FCS-D-MEM medium (a Dulbecco's MEM medium (Nissui) containing 10% fetal calf serum). The cells were dispersed into single cells by trypsin-EDTA treatment, and then a 10% FCS-D-MEM medium was added to recover the cells, followed by centrifugation at 1200 rpm for 5 minutes. After centrifugation, the cells were prepared to $1 \times 10^6$ cells/ml by a HEPES buffer (Hanks' solution (Nissui) containing 15 mM HEPES, pH 7.4), and beraprost sodium (0.1 to 30 μM) was added to the cell solution, followed by incubation at 37° C. for 30 minutes. Then, 800 μm of TBH (tertiary butyl hydroperoxide, Funakoshi) as a peroxide was added to the cell solution, followed by further incubation at 37° C. for 30 minutes. After reaction was stopped under ice cooling, some of the cells are collected, and divided into living cells and dead cells by trypan blue staining, followed by counting to determine the survival rate of the cells. The residual cells were centrifuged at 2000 rpm for 5 minutes, and then the amount of thiobarbituric acid reaction substance (TBARS amount) was measured according to the known method (Ohkawa, H., Ohnishi, N. and Yagi, K. Anal. Biochem., 95, 351–358 (1979)) and considered as an index of peroxidation of cell membrane lipid.

Figure 2:
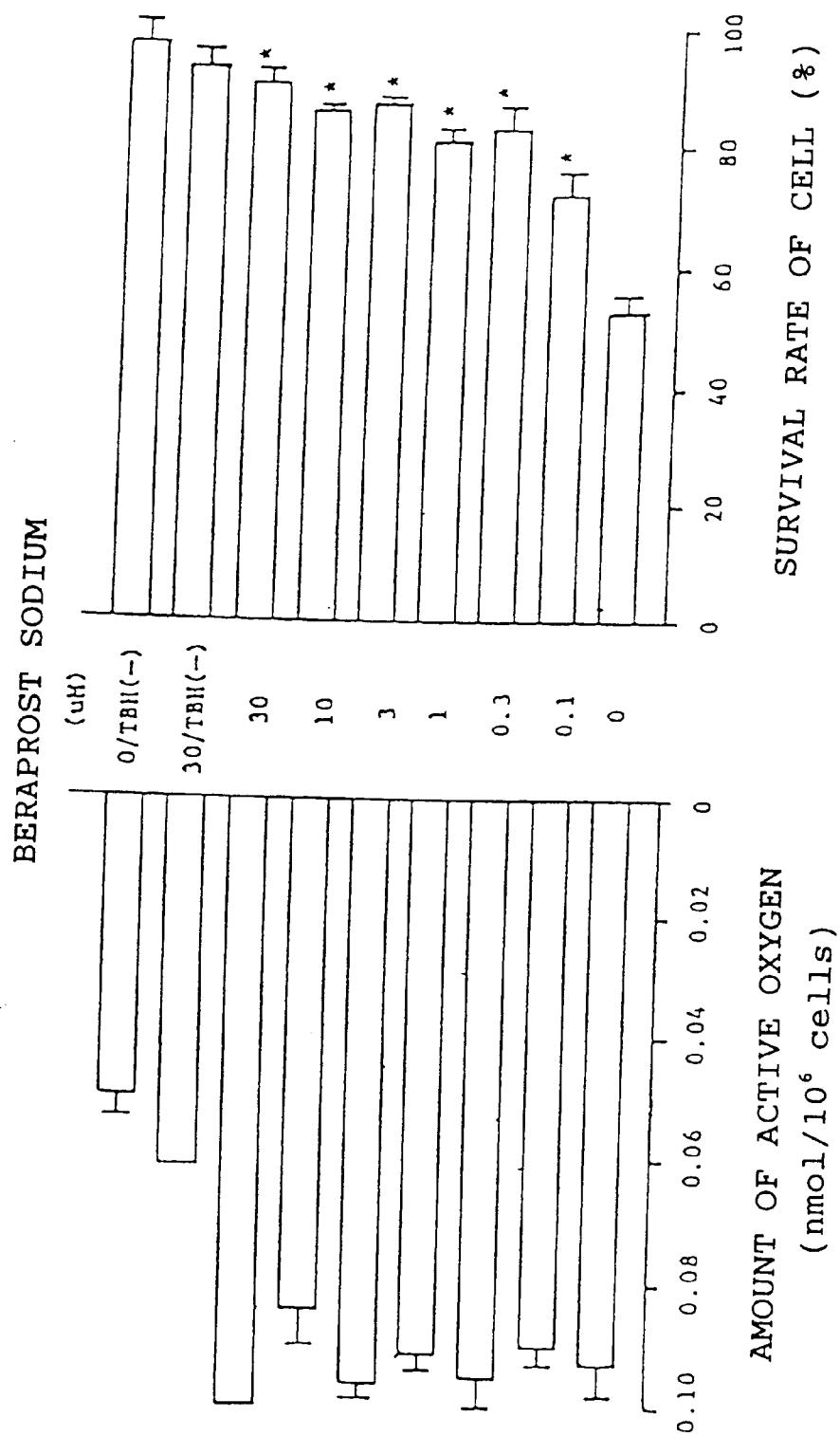
FIG. 2 is a graph showing the inhibition effect of beraprost sodium on human neuroglia stain (AIB-G) disorder due to peroxide.

The results are shown in FIG. 2. In the figure, O/TBH(−) represents TBH-untreated cells, and 30/TBH(−) represents TBH-untreated cells to which 30 M of beraprost sodium was added, the other cells being TBH-treated cells. The survival rate of human glioma cells was apparently decreased by TBH treatment, but a decrease in the survival rate of cells was significantly (p<0.01) suppressed by 0.1 $\mu$M or more of beraprost sodium. On the other hand, the TBARS amount as an index of peroxidation of cell membrane lipid was increased by TBH treatment, but beraprost sodium did not affect such an increase.

These results indicate that beraprost sodium has the cytoprotective effect on nervous system structural cells.

INDUSTRIAL APPLICABILITY

The protective agent for nervous system structural cells of the present invention has an excellent cytoprotective effect on the nervous system structural cells in either oral or parenteral administration, and is effective as an excellent agent for preventing or curing cerebrovascular disorder, cerebral neurocyte disorder, ischemic cerebral disorder, dementia, and peripheral nerve disorder due to diabetic or the like.

What is claimed is:

1. A method of protecting nervous system structural cells comprising:

administering to a patient in need thereof an effective amount of a prostaglandin I compound wherein the prostaglandin I compound is a 4,8-inter-m-phenylene prostaglandin I compound represented by the following formula (I) or a pharmacologically acceptable salt thereof

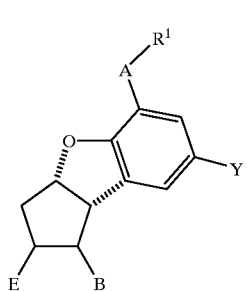

(I)

wherein $R^1$ represents the following:

(A) COOR$^2$ wherein $R^2$ is:

1) hydrogen or a pharmacologically acceptable cation;

2) straight chain alkyl having 1 to 12 carbon atoms, or branched alkyl having 3 to 14 carbon atoms;

3) —Z—R$^3$ wherein Z is a valence bond or straight chain or branched alkylene represented by $C_tH_{2t}$ wherein t represents an integer of 1 to 6, and $R^3$ represents cycloalkyl having 3 to 12 carbon atoms or substituted cycloalkyl having 3 to 12 carbon atoms and 1 to 3 substituents $R^4$ which is hydrogen or alkyl having 1 to 5 carbon atoms;

4) —(CH$_2$CH$_2$O)$_n$CH$_3$ wherein n is an integer of 1 to 5:

5) —Z—Ar$^1$ wherein Z is defined as the same as the above, and Ar$^1$ is phenyl, α-naphthyl, β-naphthyl, 2-pyridyl, 3-pyridyl, 4-pyridyl, α-furyl, β-furyl, α-thienyl, β-thienyl or substituted phenyl, wherein a substituent is at least one of chlorine, bromine, fluorine, iodine, trifluoromethyl, alkyl having 1 to 4 carbon atoms, nitro, cyano, methoxy, phenyl, phenoxy, p-acetamidobenzamide, —CH=N—NH—C(=O)—NH$_2$, —NH—C(=O)—Ph, —NH—C(=O)—CH$_3$ and —NH—C(=O)—NH$_2$;

6) —C$_t$H$_{2t}$COOR$^4$ wherein C$_t$H$_{2t}$ and $R^4$ are defined as the same as the above;

7) —C$_t$H$_{2t}$N(R$^4$)$_2$ wherein C$_t$H$_{2t}$ and $R^4$ are defined as the same as the above;

8) —CH(R$^5$)—C(=O)—R$^6$ wherein $R^5$ is hydrogen or benzoyl, and $R^6$ is phenyl, p-bromophenyl, p-chlorophenyl, p-biphenyl, p-nitrophenyl, p-benzamidophenyl, or 2-naphthyl;

9) —C$_p$H$_{2p}$—W—R$^7$ wherein W is —CH=CH—, —CH=CR$^7$ or —C≡C—, and $R^7$ is hydrogen or straight chain or branched alkyl or aralkyl having 1 to 30 carbon atoms, and p is an integer of 1 to 5; or

10) —CH(CH$_2$OR$^8$)$_2$ wherein $R^8$ is alkyl or acryl having 10 to 30 carbon atoms;

(B) —CH$_2$OH;

(C) —C(=O)N(R$^9$)$_2$ wherein $R^9$ is hydrogen, straight chain alkyl having 1 to 12 carbon atoms, branched alkyl having 3 to 12 carbon atoms, cycloalkyl having 3 to 12 carbon atoms, cycloalkylalkylene having 4 to 13 carbon atoms, phenyl, substituted phenyl, wherein the substituent is defined as the same as in (A) 5), arakyl having 7 to 12 carbon atoms, or —SO$_2$R$^{10}$ wherein $R^{10}$ is alkyl having 1 to 10 carbon atoms, cycloalkyl having 3 to 12 carbon atoms, phenyl, substituted phenyl, wherein the substituent is defined as the same as in (A) 5), or aralkyl having 7 to 12 carbon atoms, two $R^9$ groups may be the same or different, and when one of the $R^9$ groups is —SO$_2$R$^{10}$, the other $R^9$ is not —SO$_2$R$^{10}$; or (D) —CH$_2$OTHP, wherein THP is tetrahydropyranyl group;

A is the following:

1) —(CH$_2$)$_m$—;

2) —CH=CH—CH$_2$—;

3) —CH$_2$—CH=CH—;

4) —CH$_2$—O—CH$_2$—;

5) —CH=CH—;

6) —O—CH$_2$—; or

7) —C≡C—;

wherein m represents an integer of 1 to 3;

Y is hydrogen, alkyl having 1 to 4 carbon atoms, chlorine, bromine, fluorine, formyl, methoxy or nitro;

B is —X—C(R$^{11}$)(R$^{12}$)OR$^{13}$ wherein $R^{11}$ is hydrogen, alkyl having 1 to 4 carbon atoms; $R^{13}$ is hydrogen, acyl having 1 to 14 carbon atoms, aroyl having 6 to 15 carbon atoms, tetrahydropyranyl, tetrahydrofuranyl, 1-ethoxyethyl, or t-butyl; X is the following:

1) —CH$_2$—CH$_2$;

2) —CH=CH—; or

3) —C≡C; and $R^{12}$ is the following:

1) straight chain alkyl having 1 to 12 carbon atoms, or branched alkyl having 3 to 14 carbon atoms;

2) —Z—Ar² wherein Z is the defined as the same as the above, and Ar² represents phenyl, α-naphthyl, β-naphthyl, or phenyl substituted by at least one chlorine, bromine, fluorine, iodine, trifluoromethyl, alkyl having 1 to 4 carbon atoms, nitro, cyano, methoxy, phenyl or phenoxy;

3) —C$_t$H$_{2t}$OR¹⁴ wherein C$_t$H$_{2t}$ is defined as the same as the above, and R¹⁴ represents straight chain alkyl having 1 to 6 carbon atoms, branched alkyl having 3 to 6 carbon atoms, phenyl, phenyl substituted by at last one chlorine, bromine, fluorine, iodine, trifluoromethyl, alkyl having 1 to 4 carbon atoms, nitro, cyano, methoxy, phenyl or phenoxy, cyclopentyl, cyclohexyl, or cyclopentyl or cyclohexyl substituted by 1 to 4 straight chain alkyl groups having 1 to 4 carbons atoms;

4) —Z—R³ wherein Z and R³ are defined as the same as the above;

5) —C$_t$H$_{2t}$—CH=C(R¹⁵)R¹⁶ wherein C$_t$H$_{2t}$ is defined as the same as the above, and R¹⁵ and R¹⁶ each represent hydrogen, methyl, ethyl, propyl, or butyl; or 6) —C$_u$H$_{2u}$—C≡C—R¹⁷ wherein u is an integer of 1 to 7, —C$_u$H$_{2u}$ represents straight chain or branched alkylene, and R¹⁷ represents straight chain alkyl having 1 to 6 carbon atoms;

E is hydrogen or —OR¹⁸ wherein R¹⁸ represents acyl having 1 to 12 carbon atoms, aroyl having 7 to 15 carbon atoms, or R² wherein R², is defined as the same as the above; and the formula represents the d, l or dl form.

2. The method of protecting nervous system structural cells according to claim 1, wherein the nervous system structural cells are nerve cells.

3. The method of protecting nervous system structural cells according to claim 1, wherein the nervous system structural cells are neuroglia.

4. The method of claim 1, wherein said patient is suffering from a cerebrovascular disorder.

5. The method of claim 1, wherein said patient is suffering from cerebral nerve cell disorder.

6. The method of claim 1, wherein said patient is suffering from ischemic cerebral disorder.

7. The method of claim 1, wherein said patient is suffering from dementia.

8. The method of claim 1, wherein said patient is suffering from a peripheral nerve disorder.

9. The method of claim 1, wherein said peripheral nerve disorder is due to diabetes.

10. A method of suppressing death of nerve cells and glioma cells comprising:

administering to a patient in need thereof an effect amount of a prostaglandin I compound wherein the prostaglandin I compound is a 4,8-inter-m-phenylene prostaglandin I compound represented by the following formula (I) or a pharmaceutically acceptable salt thereof

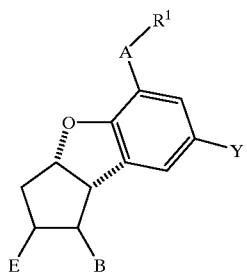

(I)

wherein R¹ represents the following:

(A) COOR² wherein R² is:

1) hydrogen or a pharmacologically acceptable cation;

2) straight chain alkyl having 1 to 12 carbon atoms, or branched alkyl having 3 to 14 carbon atoms;

3) —Z—R³ wherein Z is a valence bond or straight chain or branched alkylene represented by C$_t$H$_{2t}$ wherein t represents an integer of 1 to 6, and R³ represents cycloalkyl having 3 to 12 carbon atoms or substituted cycloalkyl having 3 to 12 carbon atoms and 1 to 3 substituents R⁴ which is hydrogen or alkyl having 1 to 5 carbon atoms;

4) —(CH₂CH₂O)$_n$CH₃ wherein n is an integer of 1 to 5:

5) —Z—Ar¹ wherein Z is defined as the same as the above, and Ar¹ is phenyl, α-naphthyl, β-naphthyl, 2-pyridyl, 3-pyridyl, 4-pyridyl, α-furyl, β-furyl, α-thienyl, β-thienyl or substituted phenyl, wherein a substituent is at least one of chlorine, bromine, fluorine, iodine, trifluoromethyl, alkyl having 1 to 4 carbon atoms, nitro, cyano, methoxy, phenyl, phenoxy, p-acetamidobenzamide, —CH=N—NH—C(=O)—NH₂, —NH—C(=O)—Ph, —NH—C(=O)—CH₃ and —NH—C(=O)—NH₂;

6) —C$_t$H$_{2t}$COOR⁴ wherein C$_t$H$_{2t}$ and R⁴ are defined as the same as the above;

7) —C$_t$H$_{2t}$N(R⁴)₂ wherein C$_t$H$_{2t}$ and R⁴ are defined as the same as the above;

8) —CH(R⁵)—C(=O)—R⁶ wherein R⁵ is hydrogen or benzoyl, and R⁶ is phenyl, p-bromophenyl, p-chlorophenyl, p-biphenyl, p-nitrophenyl, p-benzamidophenyl, or 2-naphthyl;

9) —C$_p$H$_{2p}$—W—R⁷ wherein W is —CH=CH—, —CH=CR⁷ or —C≡C—, and R⁷ is hydrogen or straight chain or branched alkyl or aralkyl having 1 to 30 carbon atoms, and p is an integer of 1 to 5; or

10) —CH(CH₂OR⁸)₂ wherein R⁸ is alkyl or acryl having 10 to 30 carbon atoms;

(B) —CH₂OH;

(C) —C(=O)N(R⁹)₂ wherein R⁹ is hydrogen, straight chain alkyl having 1 to 12 carbon atoms, branched alkyl having 3 to 12 carbon atoms, cycloalkyl having 3 to 12 carbon atoms, cycloalkylalkylene having 4 to 13 carbon atoms, phenyl, substituted phenyl, wherein the substituent is defined as the same as in (A) 5), arakyl having 7 to 12 carbon atoms, or —$SO_2R^{10}$ wherein $R^{10}$ is alkyl having 1 to 10 carbon atoms, cycloalkyl having 3 to 12 carbon atoms, phenyl, substituted phenyl, wherein the substituent is defined as the same as in (A) 5), or aralkyl having 7 to 12 carbon atoms, two $R^9$ groups may be the same or different, and when one of the $R^9$ groups is —$SO_2R^{10}$, the other $R^9$ is not —$SO_2R^{10}$; or (D) —$CH_2OTHP$, wherein THP is tetrahydropyranyl group;

A is the following:

1) —$(CH_2)_m$—;
2) —CH=CH—$CH_2$—;
3) —$CH_2$—CH=CH—;
4) —$CH_2$—O—$CH_2$—;
5) —CH=CH—;
6) —O—$CH_2$—; or
7) —C≡C—;

wherein m represents an integer of 1 to 3;

Y is hydrogen, alkyl having 1 to 4 carbon atoms, chlorine, bromine, fluorine, formyl, methoxy or nitro;

B is —X—$C(R^{11})(R^{12})OR^{13}$ wherein $R^{11}$ is hydrogen, alkyl having 1 to 4 carbon atoms; $R^{13}$ is hydrogen, acyl having 1 to 14 carbon atoms, aroyl having 6 to 15 carbon atoms, tetrahydropyranyl, tetrahydrofuranyl, 1-ethoxyethyl, or t-butyl; X is the following:

1) —$CH_2$—$CH_2$;
2) —CH=CH—; or
3) —C≡C; and $R^{12}$ is the following:

1) straight chain alkyl having 1 to 12 carbon atoms, or branched alkyl having 3 to 14 carbon atoms;

2) —Z—$Ar^2$ wherein Z is the defined as the same as the above, and $Ar^2$ represents phenyl, α-naphthyl, β-naphthyl, or phenyl substituted by at least one chlorine, bromine, fluorine, iodine, trifluoromethyl, alkyl having 1 to 4 carbon atoms, nitro, cyano, methoxy, phenyl or phenoxy;

3) —$C_tH_{2t}OR^{14}$ wherein $C_tH_{2t}$ is defined as the same as the above, and $R^{14}$ represents straight chain alkyl having 1 to 6 carbon atoms, branched alkyl having 3 to 6 carbon atoms, phenyl, phenyl substituted by at last one chlorine, bromine, fluorine, iodine, trifluoromethyl, alkyl having 1 to 4 carbon atoms, nitro, cyano, methoxy, phenyl or phenoxy, cyclopentyl, cyclohexyl, or cyclopentyl or cyclohexyl substituted by 1 to 4 straight chain alkyl groups having 1 to 4 carbons atoms;

4) —Z—$R^3$ wherein Z and $R^3$ are defined as the same as the above;

5) —$C_tHt_2$—CH=$C(R^{15})R^6$ wherein $C_tH_{2t}$ is defined as the same as the above, and $R^{15}$ and $R^{16}$ each represent hydrogen, methyl, ethyl, propyl, or butyl; or 6) —$C_uH_{2u}$—C≡C—$R^{17}$ wherein u is an integer of 1 to 7, —$C_uH_{2u}$ represents straight chain or branched alkylene, and $R^{17}$ represents straight chain alkyl having 1 to 6 carbon atoms;

E is hydrogen or —$OR^{18}$ wherein $R^{18}$ represents acyl having 1 to 12 carbon atoms, aroyl having 7 to 15 carbon atoms, or $R^2$, wherein $R^2$ is defined as the same as the above; and the formula represents the d, l or dl form.

11. The method of claim 4, 5, 6, 7, 8, 9 or 10, wherein said compound is administered to an adult, 1 to 3 times per day, in an amount of 0.01 to 100 mg/adult.

\* \* \* \* \*